United States Patent
Olson et al.

(10) Patent No.: US 11,814,436 B2
(45) Date of Patent: Nov. 14, 2023

(54) ANTI-CD30 MONOCLONAL ANTIBODIES AND CHIMERIC ANTIGEN RECEPTORS

(71) Applicant: NantBio, Inc., Culver City, CA (US)

(72) Inventors: Clifford Anders Olson, Culver City, CA (US); Kayvan Niazi, Culver City, CA (US); Helty Adisetiyo, Culver City, CA (US); Hermes J. Garban, Culver City, CA (US); Mark Guido, Culver City, CA (US); Heather McFarlane, Los Angeles, CA (US); Tan Trinh, Culver City, CA (US); Shiho Tanaka, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 0 days.

(21) Appl. No.: 17/680,174

(22) Filed: Feb. 24, 2022

(65) Prior Publication Data
US 2022/0275098 A1 Sep. 1, 2022

Related U.S. Application Data

(60) Provisional application No. 63/155,073, filed on Mar. 1, 2021.

(51) Int. Cl.
| | | |
|---|---|---|
| *C07K 16/28* | (2006.01) | |
| *A61K 39/395* | (2006.01) | |
| *C07K 14/725* | (2006.01) | |
| *C07K 14/705* | (2006.01) | |
| *C07K 14/54* | (2006.01) | |
| *C07K 14/715* | (2006.01) | |

(52) U.S. Cl.
CPC ...... *C07K 16/2878* (2013.01); *A61K 39/3955* (2013.01); *C07K 14/5443* (2013.01); *C07K 14/7051* (2013.01); *C07K 14/70517* (2013.01); *C07K 14/70521* (2013.01); *C07K 14/7155* (2013.01); *C07K 2317/31* (2013.01); *C07K 2317/56* (2013.01); *C07K 2317/622* (2013.01); *C07K 2319/30* (2013.01)

(58) Field of Classification Search
None
See application file for complete search history.

(56) References Cited

U.S. PATENT DOCUMENTS

| | | |
|---|---|---|
| 7,790,160 B2 | 9/2010 | Von Strandmann et al. |
| 10,815,301 B2 | 10/2020 | Kochenderfer |
| 2016/0200824 A1 | 7/2016 | Chmielewski et al. |
| 2019/0218293 A1 | 7/2019 | Farsaci et al. |

FOREIGN PATENT DOCUMENTS

| | | |
|---|---|---|
| CN | 112261950 A | 1/2021 |
| KR | 10-2018-0057723 A | 5/2018 |
| WO | 03/043583 A2 | 5/2003 |
| WO | 2017/066122 A1 | 4/2017 |
| WO | 2018/027022 A1 | 2/2018 |
| WO | 2020/068774 A1 | 4/2020 |
| WO | 2020/072519 A1 | 4/2020 |
| WO | 2020/135559 A1 | 7/2020 |

OTHER PUBLICATIONS

International Preliminary Report on Patentability (Chapter I) received for PCT Application Serial No. PCT/US2022/017763 dated Sep. 14, 2023, 7 pages.
"Immunoglobulin G heavy chain variable region, partial [Homo sapiens]", GenBank: AEX28629.1, Jan. 10, 2014, 2 pages.
"Immunoglobulin light chain variable region, partial [Homo sapiens]", GenBank: QRN77462.1, Feb. 17, 2021, 1 page.

*Primary Examiner* — Brad Duffy
(74) *Attorney, Agent, or Firm* — Martin Fessenmaier; Umberg Zipser LLP

(57) ABSTRACT

Antibodies, fragments thereof, and chimeric proteins comprising same are presented that have specific binding activity against CD30. Advantageously, contemplated molecules can be used in pharmaceutical compositions for immune therapy, particularly in individuals diagnosed with hematopoietic malignancies, including Hodgkin lymphoma, CD30-positive B cell lymphomas, CD30-positive T cell lymphomas, CD30-positive NK cell lymphomas.

18 Claims, 8 Drawing Sheets

Specification includes a Sequence Listing.

US 11,814,436 B2

ANTI-CD30 MONOCLONAL ANTIBODIES AND CHIMERIC ANTIGEN RECEPTORS

This application claims priority to our co-pending U.S. Provisional Patent application with the Ser. No. 63/155,073, which was filed Mar. 1, 2021, and which is incorporated by reference in its entirety.

Sequence Listing

The content of the ASCII text file of the sequence listing named 102719.0034PRO_REV002 _ST25.txt, which is 11 KB in size was created on Jan. 20, 2021 and electronically submitted via EFS-Web along with the present application, and which is incorporated by reference in its entirety.

FIELD OF THE INVENTION

The field of the invention is target specific binding molecules, especially as it relates to antibodies and chimeric antigen receptors, and derivatives thereof with binding specificity against CD30.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

CD30 (Cluster of Differentiation 30, Ki-1, TNFRSF8) belongs to the tumor necrosis factor receptor superfamily and is transiently expressed in human at relatively low levels on intrafollicular and perifollicular T and B cell blasts in lymphoid tissues. Notably, CD30 expression is significantly increased with specific hematopoietic malignancies, including anaplastic large cell lymphoma and Hodgkin lymphoma. As such, CD30 is a common diagnostic marker for malignant cells in Hodgkin's disease (HD) and a subset of non-Hodgkin's (NHL) lymphomas, such as anaplastic large cell lymphoma (ALCL). More recently, CD30 has also emerged as a therapeutic target in the treatment of various hematologic diseases, and a number of specific CD30-binding molecules have been developed.

For example, certain CD30 binding moieties and chimeric antibodies are shown in WO 2020/135559 and have been proposed for adoptive T cell therapy in the treatment of CD30 expressing cancers or tumors. Similarly, specific chimeric antigen receptors (CAR) with binding activity against CD30 and various uses for these CARs are taught in US 10,815,301, and in still another example, bispecific antibodies were constructed that bind to CD30 as shown in WO 2020/068774.

In further examples, methods of treatment of T cell lymphoma using certain anti-CD30 antibody-drug conjugates in combination with a second drug are taught in WO 2020/072519, and in yet another combination treatment, specific anti-CD30 antibodies were administered with checkpoint inhibitors to treat Hodgkin lymphoma or non-Hodgkin lymphoma as disclosed in US2019/0218293. Still further combination treatments using anti-CD30 antibodies and proteasome inhibitors are disclosed in WO 2018/027022 and U.S. Pat. No. 7,790,160, and treatment of immunological disorders other than cancer with anti-CD30 antibodies are described in WO 03/043583. While many of the known anti-CD30 binders will exhibit at least some diagnostic or therapeutic potential, various disadvantages nevertheless remain. Most significantly, the binding affinity and/or binding specificity of at least some anti-CD30 antibodies or anti-CD30 CARs is less than desirable or had less than desirable therapeutic efficacy.

Thus, even though various systems and methods of anti-CD30 antibodies and CARs are known in the art, all or almost all of them suffer from several drawbacks. Therefore, there remains a need for compositions and methods for improved anti-CD30 antibodies and CARs and uses therefor.

SUMMARY OF THE INVENTION

The inventive subject matter is directed to various compositions and methods of CD30 specific therapeutic and diagnostic molecules and their use in diagnosis and treatment of an individual, and particularly cancer where the cancer cells express or overexpress CD30.

In one aspect of the inventive subject matter, the inventors contemplate an isolated antibody or fragment thereof, wherein the antibody or fragment thereof binds to CD30 and includes a variable heavy chain (VH) domain and a variable light chain (VL) domain, wherein the VH domain is selected form the group consisting of SEQ ID NO:1, SEQ ID NO:3, and SEQ ID NO:5, and wherein the VL domain is selected form the group consisting of SEQ ID NO:2, SEQ ID NO:4, and SEQ ID NO:6.

In one embodiment, the antibody or fragment comprises VH52-2 (SEQ ID NO:1) and VL52-2 (SEQ ID NO:2), optionally coupled together by a linker to form an scFv. In another embodiment, the antibody or fragment comprises VH52-5 (SEQ ID NO:3) and VL52-5 (SEQ ID NO:4), optionally coupled together by a linker to form an scFv. In a further embodiment, the antibody or fragment comprises VH52-38 (SEQ ID NO:5) and VL52-38 (SEQ ID NO:6), optionally coupled together by a linker to form an scFv.

Most typically, but not necessarily, antibody is an IgG1 antibody or an scFv, and/or may further include a therapeutic agent (e.g., a chemotherapeutic drug, a radionuclide, or an immune stimulant such as a cytokine, a cytokine analog, a chemokine, or a checkpoint inhibitor). Alternatively, or additionally, the antibody or fragment may also comprise a detectable label.

In other embodiments, the inventors also contemplate a chimeric protein that comprises the antibody or fragment presented herein. For example, the chimeric protein may form a chimeric antigen receptor (CAR), which may have a CD3zeta (CD3ζ) or Fc receptor epsilon (FcεRIγ) signaling domain, or that may have one or more of a CD28 signaling domain, a 4-1BB signaling domain, and a CD3zeta (CD3ζ) signaling domain. Most typically, the CAR may have a CD8 hinge domain and a CD28 transmembrane domain. As will be readily appreciated, the CAR will be a recombinant CAR that is expressed in and presented on the surface of an NK cell or a cytotoxic T cell. In other examples, the chimeric protein may form a bispecific fusion protein (e.g., comprising an IgG Fc portion, and optionally further comprising at least one of an IL15α receptor portion, an IL15 portion, and an IL15 superagonist portion) or may form a bispecific killer cell engager (BiKE) or a trispecific killer cell engager (TriKe).

Therefore, the inventors also contemplate a recombinant nucleic acid that encodes the isolated antibody or fragment, or the chimeric protein presented herein. For example, the nucleic acid may be part of an expression vector or part of a recombinant viral genome or may be in form of a linear DNA. On the other hand, the recombinant nucleic acid may also be an RNA.

Viewed from a different perspective, the inventors also contemplate a pharmaceutical composition that includes a pharmaceutically acceptable carrier in combination with the isolated antibody or fragment or the chimeric protein as presented herein. Similarly, the inventors also contemplate a pharmaceutical composition that includes a pharmaceutically acceptable carrier in combination with the recombinant nucleic acid as presented herein.

In another aspect of the inventive subject matter, the inventors also a method of treating an individual, in which the pharmaceutical compositions presented herein are administered to the individual, typically to thereby reduce immune suppression in the individual. Most typically, the individual is being treated with a cancer vaccine and/or a checkpoint inhibitor. Therefore, the inventors also contemplate the use of the pharmaceutical compositions as presented herein in the treatment of a hematologic cancer in an individual.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
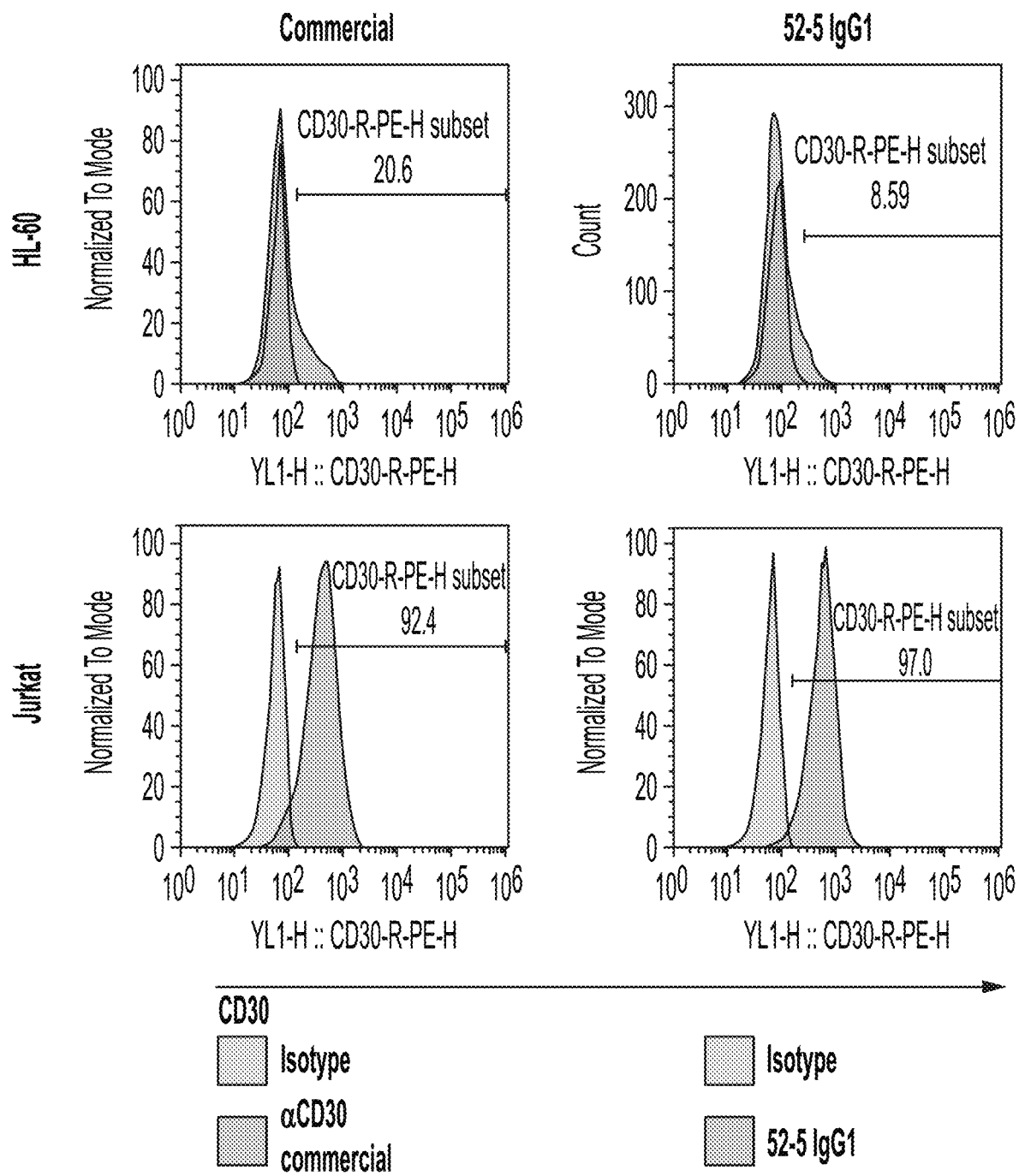
FIG. 1 is a graph depicting exemplary FACS results for anti-CD30 antibody binding on cells expressing CD30 and control cells (HL-60) using a commercially available anti-CD30 antibody and an IgG1 antibody according to the inventive subject matter.

The inventors have discovered various anti-CD30 antibodies that have high affinity and specificity with respect to binding to CD30. In particularly preferred aspects, contemplated antibodies are human $IgG_1$ antibodies that have the $V_H$ and $V_L$ domains as shown below. However, it should be appreciated that the sequences presented herein can vary to at least some degree and may therefore have one or more amino acid substitutions, insertions, and/or deletions as is discussed in more detail below. Most typically, but not necessarily, $V_H$ and $V_L$ domains, or heavy and light chains with the same preceding numeral (e.g., 52-2) will be present in a CD30 binding construct. However, other CD30 binding constructs may only have the $V_H$ or $V_L$ domain, or a $V_H$ and a $V_L$ domain with non-identical preceding numeral. Moreover, CD30 binding constructs may include those that have at least some of the CDRs (e.g., at least those from $V_H$ domain) as listed below.

52-2 $V_H$ domain amino acid sequence:
(SEQ ID NO: 1)
EVQLVESGGGLVQPGGSLRLSCAASGFTFSSYYMH

WVRQAPGKGLEWVSAISWSGGSTYYADSVKGRFTI

SRDNSKNTLYLQMNSLRAEDTAVYYCARDRFMPFI

PNTLGFDVWGQGTLVTVSS 52-2 $V_L$ domain amino acid sequence:
(SEQ ID NO: 2)
DIQMTQSPSSLSASVGDRVTITCQASQDISNYLNW

YQQKPGKAPKLLIYVASNLETGVPSRFSGSGSGTD

FTFTISSLQPEDIATYYCQQDADVPLTFGQGTKVEIK 52-5 $V_H$ domain amino acid sequence:
(SEQ ID NO: 3)
EVQLVESGGGLVQPGGSLRLSCAASGFTFSSYYMH

WVRQAPGKGLEWVSAISWSGGSTYYADSVKGRFTI

SRDNSKNTLYLQMNSLRAEDTAVYYCARDRFMPFI

PNTLGFDVWGQGTLVTVSS 52-5 $V_L$ domain amino acid sequence:
(SEQ ID NO: 4)
DIQMTQSPSSLSASVGDRVTITCQASQDISNYLNW

YQQKPGKAPKLLIYDASNLETGVPSRFSGSGSGTD

FTFTISSLQPEDIATYYCQQDADVPLTFGQGTKVEIK 52-38 $V_H$ domain amino acid sequence:
(SEQ ID NO: 5)
MEVQLVESGGGLVQPGGSLRLSCAASGFTFSSYWM

HWVRQAPGKGLEWVSAISWSGDSTYYADSVKGRFT

ISRDNSKNTLYLQMNSLRAEDTAVYYCARDRSATW

YYLGLGFDVWGQGTLVTVSS

-continued 52-38 V_L domain amino acid sequence:
(SEQ ID NO: 6)
DIQMTQSPSSLSASVGDRVTITCQASQDISNYLNW

YQQKPGKAPKLLIYDASNLETGVPSRFSGSGSGTD

FTFTISSLQPEDIATYYCQQVANVPLTFGQGTKVE

IK

As will be readily appreciated, the binding specificity of the V_H and V_L domains is dictated by their respective CDR regions, and Table 1 below shows the amino acid sequences for the CDRs in the V_H and V_L domains. Therefore, based on the known CDR sequences, it is contemplated that antibodies and fragments thereof can be prepared that bind CD30 and that include at least some of the CDRs of SEQ ID Nos: 7-24.

TABLE 1

| Clone | CDR-H1 | CDRH-2 | CDR-H3 | CDR-L1 | CDR-12 | CDR-13 |
|---|---|---|---|---|---|---|
| 52-2 | SYYMH SEQ ID NO: 7 | AISWS GGSTY YADSV KG SEQ ID NO: 8 | DRFMP FIPNT LGFDV SEQ ID NO: 9 | QASQD ISNYL N SEQ ID NO: 10 | VASNL ET SEQ ID NO: 11 | QQDAD VPLT SEQ ID NO: 12 |
| 52-5 | SYYMH SEQ ID NO: 13 | AISWS GGSTY YADSV KG SEQ ID NO: 14 | DRFMP FIPNT LGFDV SEQ ID NO: 15 | QASQD ISNYL N SEQ ID NO: 16 | DASNL ET SEQ ID NO: 17 | QQDAD VPLT SEQ ID NO: 18 |
| 52-38 | SYWMH SEQ ID NO: 19 | AISWS GDSTY YADSV KG SEQ ID NO: 20 | DRSAT WYYLG LGFDV SEQ ID NO: 21 | QASQD ISNYL N SEQ ID NO: 22 | DASNL ET SEQ ID NO: 23 | QQVAN VPLT SEQ ID NO: 24 |

For example, using the CDRs and V_H and V_L domain information above, IgG_1 antibodies can be prepared. Most typically, but not necessarily, HC and LC with the same preceding numeral (e.g., 64-6) will be present in a CD30 binding antibody. However, other CD30 binding antibodies may have a heavy chain and a light chain with non-identical preceding numeral.

Of course, it should be appreciated that the inventive subject matter is not limited to the exact sequences noted above, but one or more of the sequences may include one or more amino acid changes. Most preferably, the changes will not result in a substantial reduction of specificity and/or affinity. Thus, contemplated amino acid changes will typically be in the framework regions of the V_H and/or V_L domains, and/or in the constant regions of HC and/or LC. Viewed from a different perspective, amino acid changes will preferably not be present in the CDR region. For example, contemplated sequences will have between 98-99% identity or homology, or between 96-98% identity or homology, or between 92-96% identity or homology, or between 85-92% identity or homology, or between 75-85% identity or homology, most typically (but not necessarily) with the changed amino acids outside the CDRs. Among other options for amino acid changes, one or more amino acids can be changed to 'humanize' a non-human antibody, and/or to move to or eliminate one or more glycosylation sites.

Moreover, it should be noted that contemplated antibodies will expressly include various forms such as monoclonal antibodies, multi-specific antibodies, human antibodies, humanized antibodies, synthetic antibodies, chimeric antibodies, single domain antibodies, single-chain Fvs (scFv), single chain antibodies, disulfide-linked Fvs (sdFv), BiKes, and TriKes as is described in more detail below. Of course, it should also be noted that the term antibody expressly includes all classes of immunoglobulin molecules (e.g., IgG, IgE, IgM, IgD, IgA, and IgY), as well as the corresponding subclasses (e.g., IgG_1, IgG_2, IgG_3, IgG_4, IgA_1, IgA_2).

With respect to contemplated antibody fragments it should be noted that fragments will include one or more portions of an antibody that contains CDRs (typically all CDRs of at least one of V_H and V_L), and optionally the framework residues. Thus, antibody fragments will in most cases exhibit an ability to specifically bind to the antigen (here: an epitope of CD30). Among other fragments, especially contemplated fragments include Fab', F(ab')_2, Fv, scFv, and mutants thereof, naturally occurring variants, as well as fusion proteins with various non-antibody polypeptides (e.g., toxin, antigen recognition site for a different antigen, enzyme, receptor, receptor ligand, etc.). Viewed from a different perspective, contemplated antibody fragments will have an amino acid sequence of at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

In further contemplated aspects, the antibody of fragment thereof may be used for in vitro or in vivo diagnosis and as such be coupled to a detectable label. For example, suitable detectable labels include various enzymes, fluorescent materials, luminescent materials, bioluminescent materials, radioactive materials, positron emitting metals, and nonradioactive paramagnetic metal ions. The detectable label can be coupled or conjugated either directly to the antibody or indirectly, through an intermediate (e.g., chemical or biological linker) using techniques known in the art. Additionally, or alternatively, contemplated antibodies and fragments thereof may also be coupled to a solid support, which is particularly useful for immunoassays or purification of CD30 or cells expressing CD30. For example, suitable supports include magnetic beads, glass, cellulose, polyacrylamide, nylon, polystyrene, polyvinyl chloride, and polypropylene.

Contemplated antibodies and fragments thereof may also be coupled to or comprise a therapeutic agent to target the agent to a cell expressing CD30. For example, especially contemplated therapeutic agents include chemotherapeutic drugs, radionuclide, and immune stimulants (e.g., cytokine, a cytokine analog, a chemokine, or a checkpoint inhibitor). There are numerous manners of preparing antibody-drug conjugates, and all of these are deemed suitable for use herein.

In especially preferred aspects, contemplated antibodies or fragments thereof may also be prepared as chimeric proteins in which at least one portion of the antibody is continuous with a second polypeptide (optionally via a preferably flexible linker). For example, suitable chimeric proteins may be configured as chimeric antigen receptors (CAR) that may have an intracellular signaling portion, a transmembrane portion, and an extracellular recognition domain. In such case, it is generally contemplated that the recognition domain includes an antibody fragment (e.g., scFv or single domain) and/or that the intracellular signaling domain comprises an activating/ITAM motif. Among other options, contemplated may be first, second, or third generation CARs with a variety of domains known in the art. For example, suitable CARS will include a CD8 hinge portion, a CD28 transmembrane domain, and a CD3zeta (CD3ζ) or Fc receptor epsilon (FcεRIγ) signaling domain. Alternatively, the signaling domain may also include one or more of a CD28 signaling domain, a 4-1BB signaling domain, and a CD3zeta (CD3ζ) signaling domain. Among other options, such chimeric antigen receptors are preferably expressed in cytotoxic immune competent cells, and especially in NK cells and/or T cells.

On the other hand, and especially where the anti-CD30 antibody or fragment thereof is used to additionally mediate cell or receptor/ligand contact, contemplated chimeric proteins may be constructed as a bispecific fusion protein, as a bispecific killer cell engager (BiKE), or as a trispecific killer cell engager (TriKe). For example, a bispecific fusion protein may comprise the anti-CD30 antibody or portion thereof and a second affinity ligand that selectively binds to a desired target. Such target may be a soluble protein or a cell-bound protein, and especially contemplated targets include PD-L1. On the other hand, contemplated chimeric molecules may be constructed as bispecific polypeptides (e.g., first scFv coupled via linker to second scFv) in which one portion comprises the anti-CD30 antibody or portion thereof and in which the other portion has a binder to a marker specific for an immune competent cell (e.g., anti-CD3).

In further contemplated aspects, the anti-CD30 antibody or portion thereof may also be coupled to an IgG-Fc/IL15Rα/IL15 hybrid (e.g., ALT803). For example, the anti-CD30 antibody fragment could be a scFv portion that is coupled to one or both arms of the hybrid to so form a TxM (see TxM technology at URL:Altorbioscience.com). Or the anti-CD30 antibody fragment could be a scFv portion that is coupled to one arm of the hybrid, while the other arm of the hybrid could be a scFv portion that binds PD-L1 (or other immune related ligand).

As should be appreciated, nucleic acids encoding contemplated anti-CD30 antibodies are also expressly considered herein, and the skilled artisan will be readily able to prepare such nucleic acids (e.g., DNA, RNA) and recombinant entities comprising such nucleic acids. Among other options, suitable recombinant entities include yeast, bacterial, and viral expression vectors, linear DNA for genome editing or other integration, RNA, etc. of course, it should be recognized that the recombinant nucleic acids will include suitable regulatory elements to allow for expression of the recombinant construct. Moreover, it should be noted that the nucleic acid will typically make use of codon-optimization with respect to the host cells that include and express the recombinant nucleic acid.

As will be readily appreciated, use of anti-CD30 antibodies, fragments thereof, or chimeric proteins containing anti-CD30 antibodies or fragments thereof is particularly advantageous where CD30 positive tumor cells are to be targeted, with an anti-CD30 antibody and/or an anti-CD30 CAR on a cytotoxic immune cell. Moreover, where cancer cells express and display CD30, the cells may offer a further therapeutic target (e.g., via targeting with a chimeric molecule that has a CD30 binding portion and an immune stimulatory portion (e.g., ALT-803)).

In view of these findings, the inventors also contemplate use of various recombinant CD30 binding molecules such as antibodies and fragments thereof as well as cells expressing anti-CD30 CAR molecules and pharmaceutical compositions comprising same. Most typically, such recombinant proteins may be soluble forms of antibodies and fragments thereof, soluble chimeric molecules comprising a CD30 binding portion, or membrane bound molecules such as CAR comprising a CD30 binding portion. For example, recombinant CD30 binding CARs may be expressed in a cytotoxic cell such as a T cell, a natural killer cell, or an NKT cell.

It is contemplated that such prepared or generated pharmaceutical composition can be administered to a patient having a tumor to increase effectiveness of immune therapy to so treat the tumor (e.g., to modulate (e.g., reduce, abrogate, etc.) immune suppression by the tumor, to reduce the tumor size, etc.). In some embodiments, pharmaceutical composition and/or the tumor vaccine can be administered via systemic injection including subcutaneous, subdermal injection, or intravenous injection. In other embodiments, where the systemic injection may not be efficient (e.g., for brain tumors, etc.) or more localized treatment is desired, it is contemplated that the recombinant immunoglobulin protein complex and/or pharmaceutical compositions can be administered via intratumoral injection. As used herein, the term "administering" refers to both direct and indirect administration of the compounds and compositions contemplated herein, where direct administration is typically performed by a health care professional (e.g., physician, nurse, etc.), while indirect administration typically includes a step of providing or making the compounds and compositions available to the health care professional for direct administration.

With respect to dose and schedule of the administration, it is contemplated that the dose and/or schedule may vary depending on depending on the type of protein, protein complex, or the type of the pharmaceutical composition (e.g., virus, bacteria, yeast, in combination with recombinant protein complex, etc.), type and prognosis of disease (e.g., tumor type, size, location), health status of the patient (e.g., including age, gender, etc.). While it may vary, the dose and schedule may be selected and regulated such that the formulation does not provide any significant toxic effect to the host normal cells, yet sufficient to be reduce immune suppression by reduced T cell differentiation and/or activation in the tumor microenvironment. Thus, in a preferred embodiment, an optimal or desired condition of administering the formulation can be determined based on a predetermined threshold. For example, the predetermined threshold may be a predetermined local or systemic concentration of T-cell activating, or T-cell released cytokines (e.g., IL-2, IL-12, IFN-γ, IL-12, IL-23, IL-1b, IL-6, or TGF-β, etc.) in the tumor microenvironment. Therefore, administration conditions are typically adjusted to have one or more of those cytokines increased in the tumor microenvironment at least 20%, at least 30%, at least 50%, at least 60%, at least 70% at least for 24 hours, 48 hours, 72 hours, 7 days, etc. Moreover, it is contemplated that the compounds and compositions presented herein may be co-administered (contemporaneously or sequentially) with NK cells. For example, suitable NK cells include autologous NK cells as well as NK92 cells and derivatives thereof (e.g., aNK cells, haNK cells, taNK cells, al commercially available from NantKwest, 9920 Jefferson Blvd. Culver City, CA 90232).

EXAMPLES

Using the $V_H$ and $V_L$ domains as noted above, the inventors prepared various CD30 binding constructs, and exemplary results for scFv and IgG1 constructs are shown below. For example, Table 2 below shows exemplary results for determination of dissociation constants for scFv and IgG1 constructs using the $V_H$ and $V_L$ domains as noted in the table. More specifically, $K_D$ determination was done by SPR, and average values are shown in x $10^{-9}$ M. Measurements were at 25° C. pH 7.4 with scFv or IgG1 captured on the chip surface, and CD30 was the analyte.

TABLE 2

| aCD30 clone | scFv | IgG1 |
|---|---|---|
| 52-2 | 0.8 | 3.0 |
| 52-5 | 27.1 | 22.3 |
| 52-38 | 0.77 | 2.5 |

Figure 2:
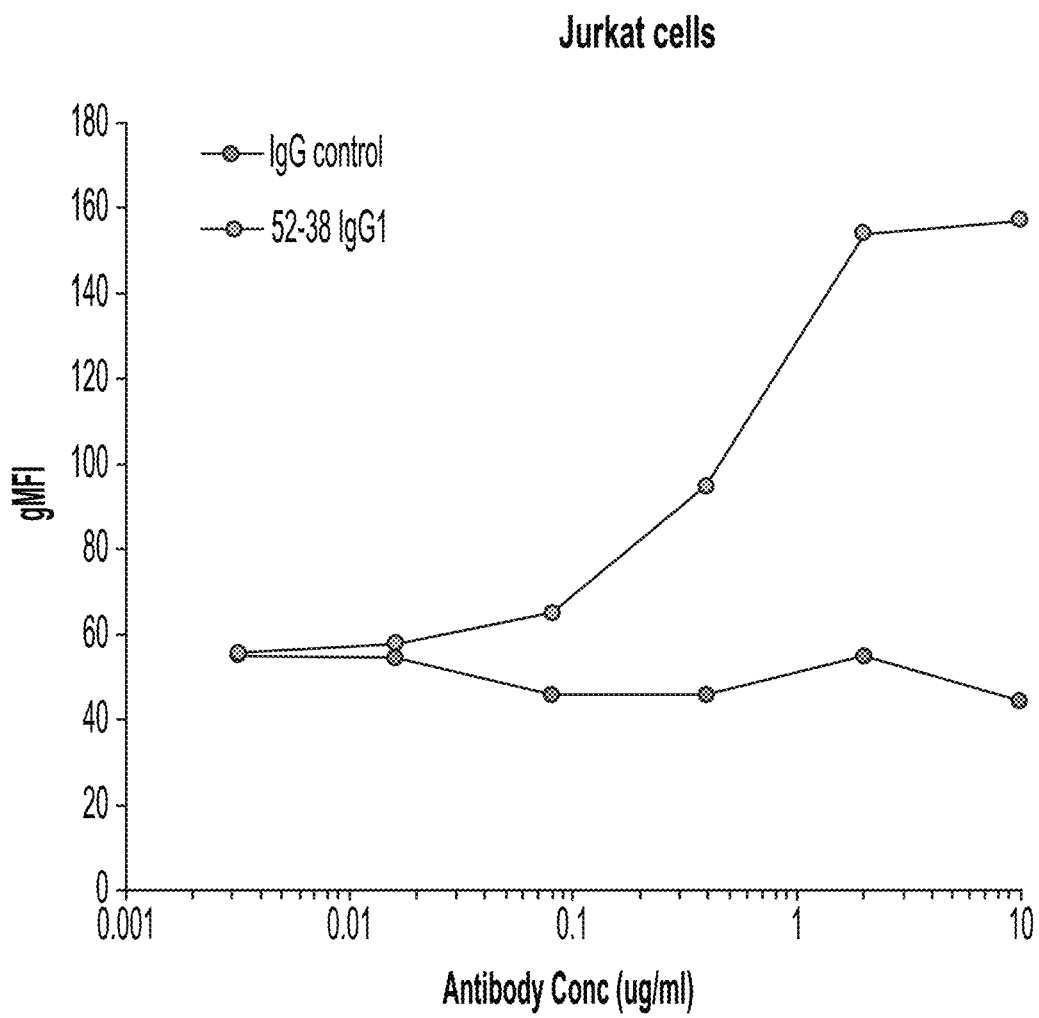
FIG. 2 is a graph depicting exemplary titration results for anti-CD30 antibody binding on cells expressing CD30 and control cells (HL-60) using a commercially available anti-CD30 antibody and an IgG1 antibody according to the inventive subject matter.

To demonstrate in vitro binding of anti-CD30 constructs to cells expressing CD30, the inventors constructed and used an anti-CD30 IgG1 (52-5) and exposed cells expressing CD30 (here: Jurkat lymphoma cells) to the anti-CD30 IgG1 antibodies, along with a commercially available anti-CD30 antibody. HL-60 cells not expressing CD30 served as negative control. As can be readily seen from the flow cytometry results in FIG. 1, the anti-CD30 IgG1 (52-5) strongly and specifically bound to Jurkat cells and exhibited substantially no binding to HL-60 cells. Moreover, binding of the anti-CD30 IgG1 (52-5) was stronger than the commercially available anti-CD30 antibody. When binding was titrated against Jurkat cells using the anti-CD30 IgG1 (52-38), a dose response curve was obtained as can be seen from FIG. 2 whereas the IgG control afforded no significant binding.

Figure 3:
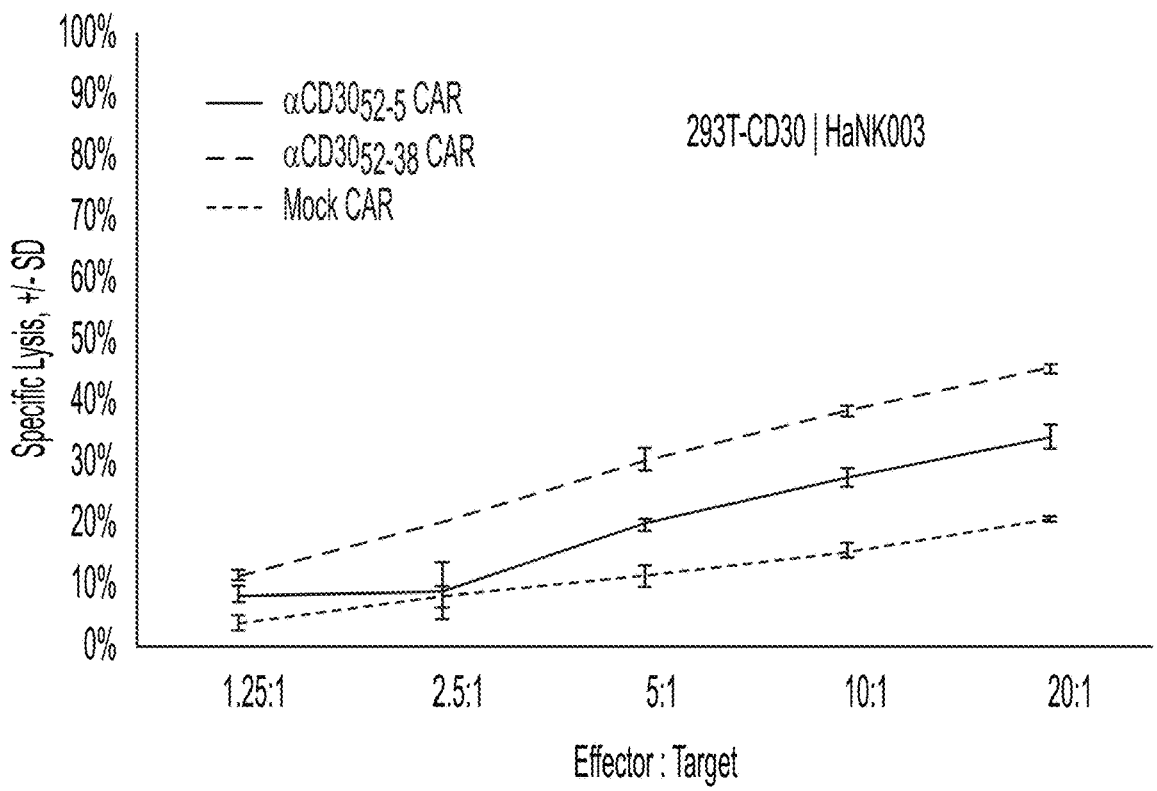
FIG. 3 is a graph depicting exemplary results for CAR specific target cell lysis of CD30 expressing target cells using haNK cells expressing exemplary anti-CD30 CAR constructs according to the inventive subject matter and a mock CAR.
Figure 4:
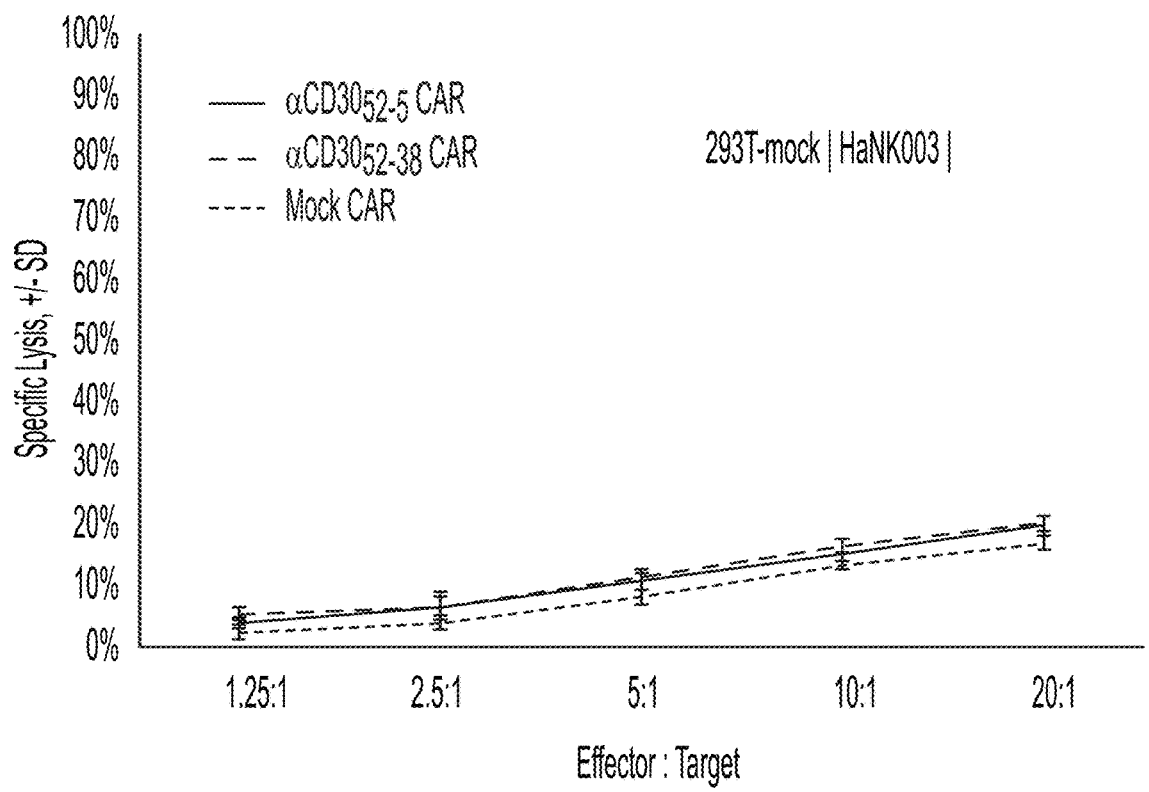
FIG. 4 is a graph depicting exemplary results for CAR specific target cell lysis of control target cells not expressing CD30 using haNK cells expressing exemplary anti-CD30 CAR constructs according to the inventive subject matter and a mock CAR.
Figure 5:
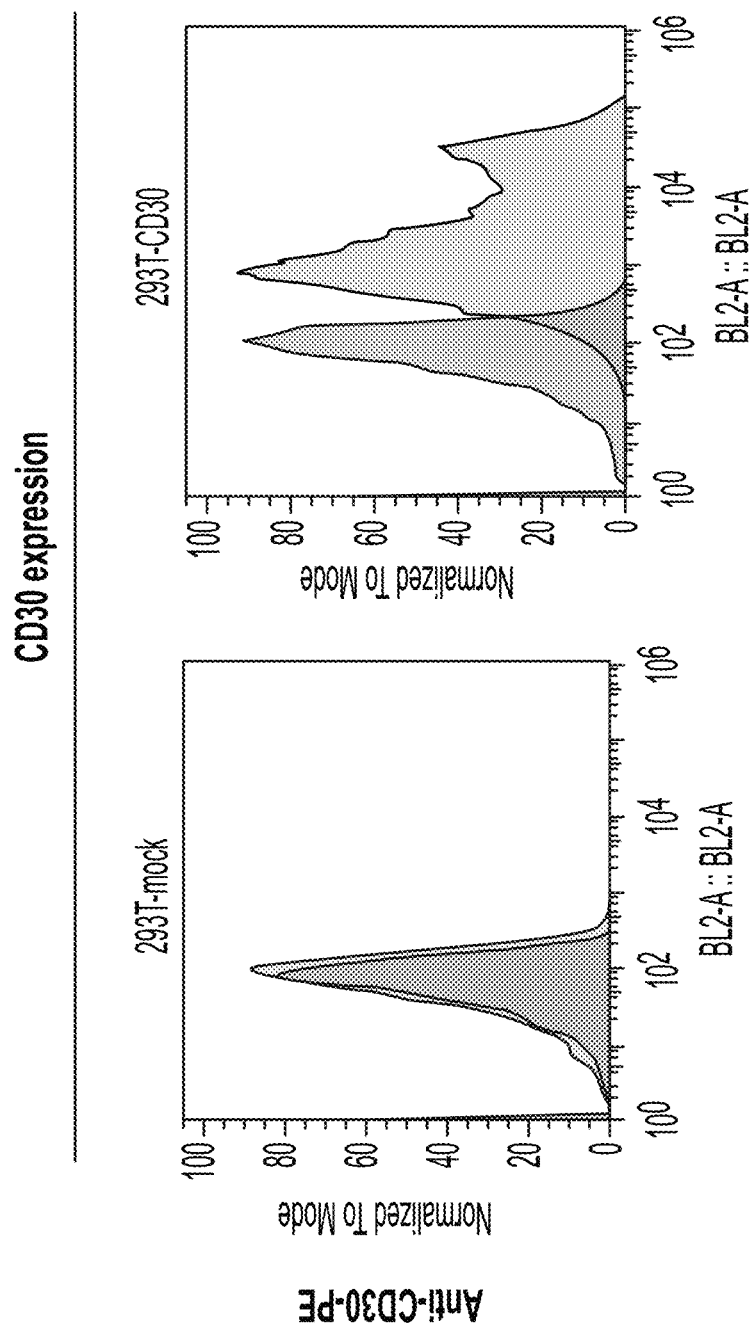
FIG. 5 is a graph depicting exemplary results for CD30 expression in the target cells of FIGS. 3 and 4.
Figure 6:
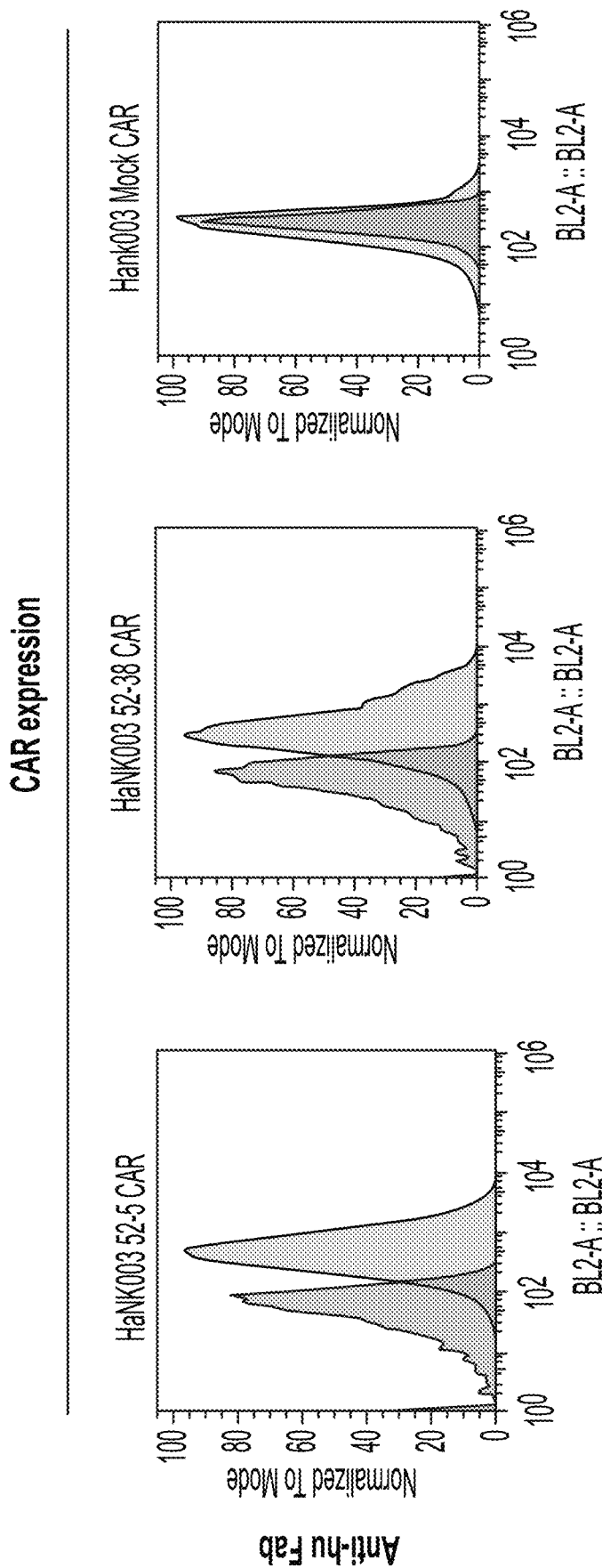
FIG. 6 is a graph depicting exemplary results for anti-CD30 CAR and mock CAR expression in the haNK cells of FIGS. 3 and 4

In a series of further experiments, the inventors constructed an anti-CD30 CAR that included an scFv portion with the $V_L$ and $V_H$ domains as noted above (coupled by a flexible linker portion), and that further included a CD8 hinge portion, a CD28 transmembrane portion, and an Fc receptor epsilon (FcεRIγ) signaling domain. FIG. 3 is a graph depicting exemplary results for CAR specific target cell lysis of CD30 expressing target cells using haNK cells expressing the anti-CD30 CAR constructs as noted and a mock CAR. FIG. 4 is a graph depicting corresponding exemplary results for CAR specific target cell lysis of control target cells not expressing CD30. FIG. 5 is a graph depicting exemplary results for CD30 expression in the target cells of FIGS. 3 and 4, and FIG. 6 is a graph depicting exemplary results for anti-CD30 CAR and mock CAR expression in the haNK cells of FIGS. 3 and 4.

Figure 7:
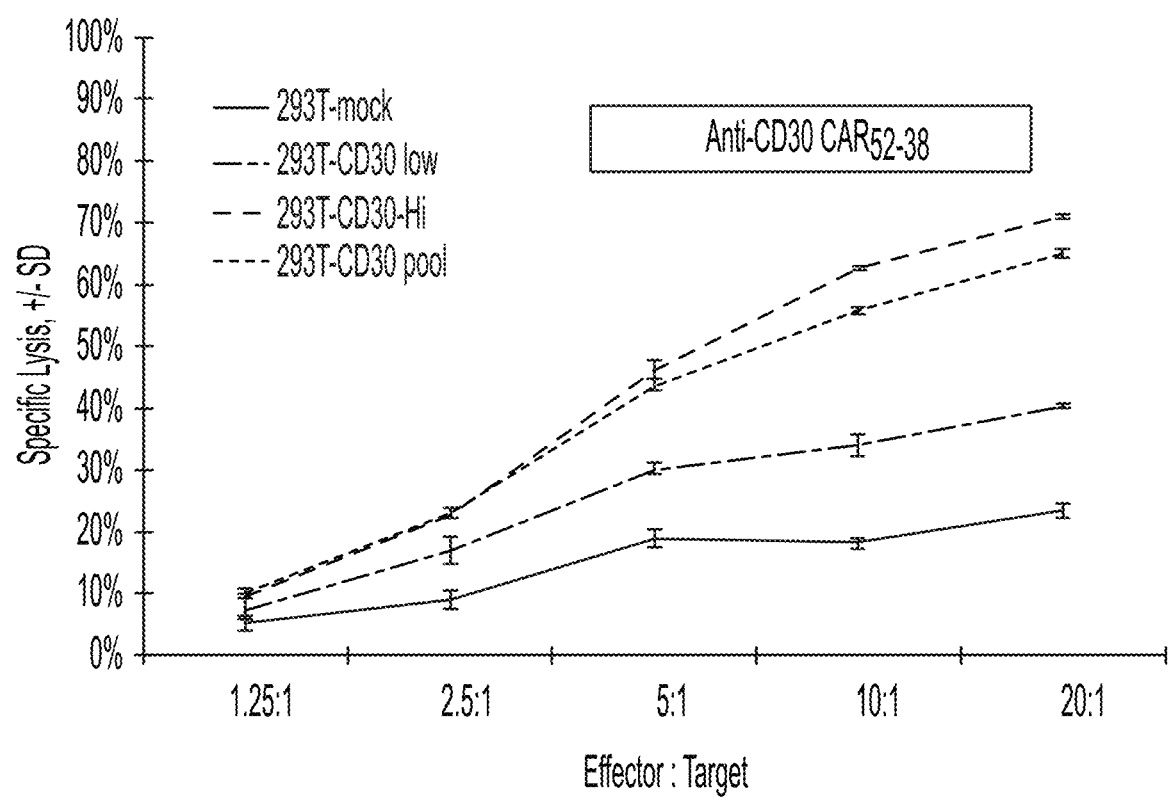
FIG. 7 is a graph depicting exemplary results for CAR specific target cell lysis of CD30 expressing target cells (low, high, pool) using haNK cells expressing another exemplary anti-CD30 CAR construct according to the inventive subject matter and a mock CAR.
Figure 8:
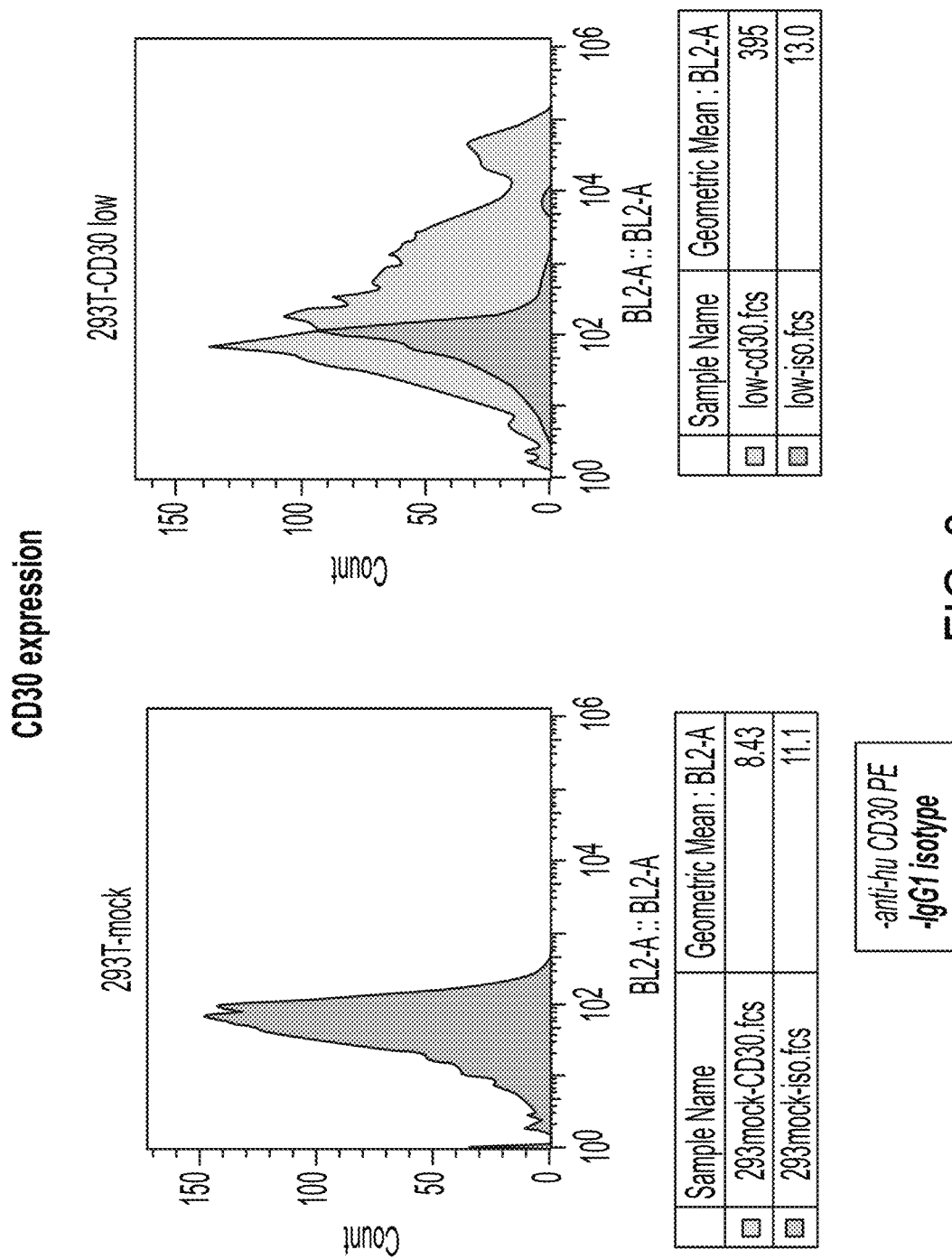
FIG. 8 is a graph depicting exemplary results for CD30 expression in the target cells of FIG. 7.
Figure 8:
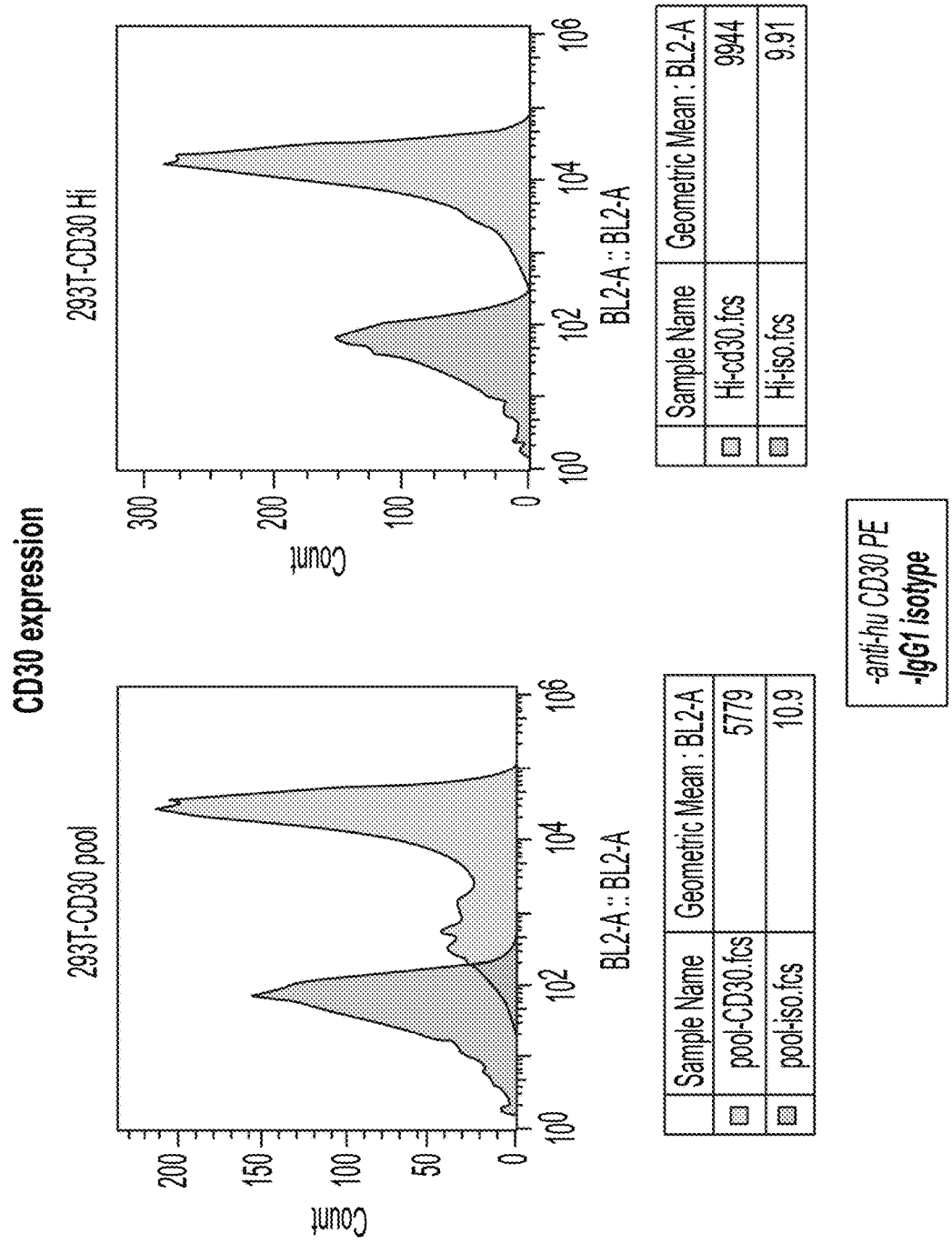

Notably, the CAR mediated cytotoxicity correlated strictly with the quantity of CD30 present on the target cells as can be seen from FIG. 7. Here, CAR specific target cell lysis of CD30 expressing target cells is shown for cells with low and high expression levels for CD30 as well as a pool of these cells. FIG. 8 exemplarily depicts results for CD30 expression in the target cells of FIG. 7.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An isolated antibody or fragment thereof, wherein the antibody or fragment thereof binds to CD30, the antibody or fragment thereof comprising:
   a variable heavy chain (VH) domain and a variable light chain (VL) domain;
   wherein the VH domain comprises an amino acid sequence selected from the group consisting of SEQ ID NO: 1, SEQ ID NO:3, and SEQ ID NO:5; and
   wherein the VL domain comprises an amino acid sequence selected from the group consisting of SEQ ID NO:2, SEQ ID NO:4, and SEQ ID NO:6.

2. The antibody or fragment of claim 1, comprising a VH comprising the amino acid sequence of SEQ ID NO:1 and a VL comprising the amino acid sequence of SEQ ID NO:2, wherein the fragment is optionally coupled together by a linker to form an scFv.

3. The antibody or fragment of claim 1, comprising a VH comprising the amino acid sequence of SEQ ID NO:3 and a VL comprising the amino acid sequence of SEQ ID NO:4, wherein the fragment is optionally coupled together by a linker to form an scFv.

4. The antibody or fragment of claim 1, comprising a VH comprising the amino acid sequence of SEQ ID NO:5 and a VL comprising the amino acid sequence of SEQ ID NO:6, wherein the fragment is optionally coupled together by a linker to form an scFv.

5. The antibody or fragment of claim 1, wherein the antibody is an $IgG_1$ antibody or an scFv.

6. The antibody or fragment of claim 1, further comprising a therapeutic agent.

7. The antibody or fragment of claim 6, wherein the therapeutic agent is a chemotherapeutic drug, a radionuclide, or an immune stimulant.

8. The antibody or fragment of claim 7, wherein the immune stimulant is a cytokine, a cytokine analog, a chemokine, or a checkpoint inhibitor.

9. The antibody or fragment of claim 1, further comprising a detectable label.

10. A chimeric protein comprising the antibody or fragment of claim 1.

11. The chimeric protein of claim 10, wherein the chimeric protein is a chimeric antigen receptor (CAR).

12. The chimeric protein of claim 11, wherein the CAR has a CD3zeta (CD3ζ) or Fc receptor epsilon (FcεRIγ) signaling domain.

13. The chimeric protein of claim 11, wherein the CAR has at least one of a CD28 signaling domain, a 4-1BB signaling domain, and a CD3zeta (CD3ζ) signaling domain.

14. The chimeric protein of claim 11, wherein the CAR has a CD8 hinge domain and a CD28 transmembrane domain.

15. The chimeric protein of claim 11, wherein the CAR is a recombinant CAR expressed in and coupled to a surface of an NK cell or a cytotoxic T cell.

16. The chimeric protein of claim 10 configured as a bispecific fusion protein.

17. The chimeric protein of claim 16 wherein the bispecific fusion protein comprises an IgG Fc portion, and optionally further comprises at least one of an IL15α receptor portion, an IL15 portion, and an IL15 superagonist portion.

18. The chimeric protein of claim 16 configured as a bispecific killer cell engager (BiKE) or a trispecific killer cell engager (TriKe).

* * * * *

SEQUENCE LISTING

<160> NUMBER OF SEQ ID NOS: 24

<210> SEQ ID NO 1
<211> LENGTH: 124
<212> TYPE: PRT
<213> ORGANISM: Artificial Sequence
<220> FEATURE:
<223> OTHER INFORMATION: 52-2 VH amino acid sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met His Trp Val Arg Gln Ala Pro Gly Lys Gly Leu Glu Trp Val
        35                  40                  45

Ser Ala Ile Ser Trp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Phe Met Pro Phe Ile Pro Asn Thr Leu Gly Phe Asp
            100                 105                 110

Val Trp Gly Gln Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: 52-2 VL amino acid sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Val Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Ala Asp Val Pro Leu
                85                  90                  95

Thr Phe Gly Gln Gly Thr Lys Val Glu Ile Lys
            100                 105

<210> SEQ ID NO 3
<211> LENGTH: 124
<212> TYPE: PRT
<213> ORGANISM: Artificial Sequence
<220> FEATURE:
<223> OTHER INFORMATION: 52-5 VH amino acid sequence

<400> SEQUENCE: 3

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
        20                  25                  30

Tyr Met His Trp Val Arg Gln Ala Pro Gly Lys Gly Leu Glu Trp Val
        35                  40                  45

Ser Ala Ile Ser Trp Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Phe Met Pro Phe Ile Pro Asn Thr Leu Gly Phe Asp
                100                 105                 110

Val Trp Gly Gln Gly Thr Leu Val Thr Val Ser Ser
        115                 120
```

```
<210> SEQ ID NO 4
<211> LENGTH: 107
<212> TYPE: PRT
<213> ORGANISM: Artificial Sequence
<220> FEATURE:
<223> OTHER INFORMATION: 52-5 VL amino acid sequence

<400> SEQUENCE: 4

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
        20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Asp Ala Asp Val Pro Leu
                 85                  90                  95

Thr Phe Gly Gln Gly Thr Lys Val Glu Ile Lys
                100                 105
```

```
<210> SEQ ID NO 5
<211> LENGTH: 125
<212> TYPE: PRT
<213> ORGANISM: Artificial Sequence
<220> FEATURE:
<223> OTHER INFORMATION: 52-38 VH amino acid sequence

<400> SEQUENCE: 5

Met Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser Ser
        20                  25                  30

Tyr Trp Met His Trp Val Arg Gln Ala Pro Gly Lys Gly Leu Glu Trp
        35                  40                  45

Val Ser Ala Ile Ser Trp Ser Gly Asp Ser Thr Tyr Tyr Ala Asp Ser
 50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
```

```
                    85                  90                  95
Cys Ala Arg Asp Arg Ser Ala Thr Trp Tyr Tyr Leu Gly Leu Gly Phe
            100                 105                 110
Asp Val Trp Gly Gln Gly Thr Leu Val Thr Val Ser Ser
            115                 120                 125

<210> SEQ ID NO 6
<211> LENGTH: 107
<212> TYPE: PRT
<213> ORGANISM: Artificial Sequence
<220> FEATURE:
<223> OTHER INFORMATION: 52-38 VL amino acid sequence

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Val Ala Asn Val Pro Leu
                85                  90                  95

Thr Phe Gly Gln Gly Thr Lys Val Glu Ile Lys
            100                 105

<210> SEQ ID NO 7
<211> LENGTH: 5
<212> TYPE: PRT
<213> ORGANISM: Artificial Sequence
<220> FEATURE:
<223> OTHER INFORMATION: 52-2 CDR-H1

<400> SEQUENCE: 7

Ser Tyr Tyr Met His
1               5

<210> SEQ ID NO 8
<211> LENGTH: 17
<212> TYPE: PRT
<213> ORGANISM: Artificial Sequence
<220> FEATURE:
<223> OTHER INFORMATION: 52-2 CDR-H2

<400> SEQUENCE: 8

Ala Ile Ser Trp Ser Gly Gly Ser Thr Tyr Tyr Ala Asp Ser Val Lys
1               5                   10                  15

Gly

<210> SEQ ID NO 9
<211> LENGTH: 15
<212> TYPE: PRT
<213> ORGANISM: Artificial Sequence
<220> FEATURE:
<223> OTHER INFORMATION: 52-2 CDR-H3

<400> SEQUENCE: 9

Asp Arg Phe Met Pro Phe Ile Pro Asn Thr Leu Gly Phe Asp Val
1               5                   10                  15
```

```
<210> SEQ ID NO 10
<211> LENGTH: 11
<212> TYPE: PRT
<213> ORGANISM: Artificial Sequence
<220> FEATURE:
<223> OTHER INFORMATION: 52-2 CDR-L1

<400> SEQUENCE: 10

Gln Ala Ser Gln Asp Ile Ser Asn Tyr Leu Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: 52-2 CDR-L2

<400> SEQUENCE: 11

Val Ala Ser Asn Leu Glu Thr
1               5

<210> SEQ ID NO 12
<211> LENGTH: 9
<212> TYPE: PRT
<213> ORGANISM: Artificial Sequence
<220> FEATURE:
<223> OTHER INFORMATION: 52-2 CDR-L3

<400> SEQUENCE: 12

Gln Gln Asp Ala Asp Val Pro Leu Thr
1               5

<210> SEQ ID NO 13
<211> LENGTH: 5
<212> TYPE: PRT
<213> ORGANISM: Artificial Sequence
<220> FEATURE:
<223> OTHER INFORMATION: 52-5 CDR-H1

<400> SEQUENCE: 13

Ser Tyr Tyr Met His
1               5

<210> SEQ ID NO 14
<211> LENGTH: 17
<212> TYPE: PRT
<213> ORGANISM: Artificial Sequence
<220> FEATURE:
<223> OTHER INFORMATION: 52-5 CDR-H2

<400> SEQUENCE: 14

Ala Ile Ser Trp Ser Gly Gly Ser Thr Tyr Tyr Ala Asp Ser Val Lys
1               5                   10                  15

Gly

<210> SEQ ID NO 15
<211> LENGTH: 15
<212> TYPE: PRT
<213> ORGANISM: Artificial Sequence
<220> FEATURE:
<223> OTHER INFORMATION: 52-5 CDR-H3

<400> SEQUENCE: 15

Asp Arg Phe Met Pro Phe Ile Pro Asn Thr Leu Gly Phe Asp Val
```

```
<210> SEQ ID NO 16
<211> LENGTH: 11
<212> TYPE: PRT
<213> ORGANISM: Artificial Sequence
<220> FEATURE:
<223> OTHER INFORMATION: 52-5 CDR-L1

<400> SEQUENCE: 16

Gln Ala Ser Gln Asp Ile Ser Asn Tyr Leu Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: 52-5 CDR-L2

<400> SEQUENCE: 17

Asp Ala Ser Asn Leu Glu Thr
1               5

<210> SEQ ID NO 18
<211> LENGTH: 9
<212> TYPE: PRT
<213> ORGANISM: Artificial Sequence
<220> FEATURE:
<223> OTHER INFORMATION: 52-5 CDR-L3

<400> SEQUENCE: 18

Gln Gln Asp Ala Asp Val Pro Leu Thr
1               5

<210> SEQ ID NO 19
<211> LENGTH: 5
<212> TYPE: PRT
<213> ORGANISM: Artificial Sequence
<220> FEATURE:
<223> OTHER INFORMATION: 52-38 CDR-H1

<400> SEQUENCE: 19

Ser Tyr Trp Met His
1               5

<210> SEQ ID NO 20
<211> LENGTH: 17
<212> TYPE: PRT
<213> ORGANISM: Artificial Sequence
<220> FEATURE:
<223> OTHER INFORMATION: 52-38 CDR-H2

<400> SEQUENCE: 20

Ala Ile Ser Trp Ser Gly Asp Ser Thr Tyr Tyr Ala Asp Ser Val Lys
1               5                   10                  15

Gly

<210> SEQ ID NO 21
<211> LENGTH: 15
<212> TYPE: PRT
<213> ORGANISM: Artificial Sequence
<220> FEATURE:
<223> OTHER INFORMATION: 52-38 CDR-H3

<400> SEQUENCE: 21
```

```
Asp Arg Ser Ala Thr Trp Tyr Tyr Leu Gly Leu Gly Phe Asp Val
1               5                   10                  15

<210> SEQ ID NO 22
<211> LENGTH: 11
<212> TYPE: PRT
<213> ORGANISM: Artificial Sequence
<220> FEATURE:
<223> OTHER INFORMATION: 52-38 CDR-L1

<400> SEQUENCE: 22

Gln Ala Ser Gln Asp Ile Ser Asn Tyr Leu Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: 52-38 CDR-L2

<400> SEQUENCE: 23

Asp Ala Ser Asn Leu Glu Thr
1               5

<210> SEQ ID NO 24
<211> LENGTH: 9
<212> TYPE: PRT
<213> ORGANISM: Artificial Sequence
<220> FEATURE:
<223> OTHER INFORMATION: 52-38 CDR-L3

<400> SEQUENCE: 24

Gln Gln Val Ala Asn Val Pro Leu Thr
1               5
```